United States Patent
Nose et al.

(10) Patent No.: US 8,420,872 B2
(45) Date of Patent: Apr. 16, 2013

(54) PROCESS FOR PREPARING FLUORINE-CONTAINING PROPENE BY GAS-PHASE FLUORINATION

(75) Inventors: Masatoshi Nose, Settsu (JP); Akinari Sugiyama, Settsu (JP); Atsushi Suzuki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 121 days.

(21) Appl. No.: 13/054,831

(22) PCT Filed: Jun. 25, 2009

(86) PCT No.: PCT/JP2009/062072
§ 371 (c)(1),
(2), (4) Date: Jan. 19, 2011

(87) PCT Pub. No.: WO2010/013577
PCT Pub. Date: Feb. 4, 2010

(65) Prior Publication Data
US 2011/0124929 A1    May 26, 2011

Related U.S. Application Data

(60) Provisional application No. 61/084,361, filed on Jul. 29, 2008, provisional application No. 61/084,364, filed on Jul. 29, 2008.

(51) Int. Cl.
*C07C 17/00* (2006.01)

(52) U.S. Cl.
USPC ........................................................ 570/161

(58) Field of Classification Search .................. 570/161
See application file for complete search history.

(56) References Cited

U.S. PATENT DOCUMENTS

| 2010/0022808 A1 | 1/2010 | Rao et al. |
| 2010/0051852 A1 | 3/2010 | Rao et al. |
| 2010/0168482 A1 | 7/2010 | Rao et al. |

FOREIGN PATENT DOCUMENTS

| JP | 8-169850 | 7/1996 |
| WO | 2008/054782 | 5/2008 |
| WO | 2008/060612 | 5/2008 |
| WO | 2008/060614 | 5/2008 |

OTHER PUBLICATIONS

International Search Report issued Sep. 17, 2009 in International (PCT) Application No. PCT/JP2009/062072.
PCT Written Opinion of the International Searching Authority issued Sep. 17, 2009 in International (PCT) Application No. PCT/JP2009/062072.
Albert L. Henne et al., "Fluorinated Derivatives of Propane and Propylene. VI." Journal of the American Chemical Society, vol. 68, pp. 496-497, 1946.
Albert L. Henne et al., "A New Method of Synthesizing Organic 1,1,1-Trifluorides," Journal of the American Chemical Society, vol. 63, pp. 3478-3479, 1941.
Oldrich Paleta et al., "Synthesis of <<Perfluoroallylchloride>> and Some Chlorofluoropropenes," Bulletin de la Société Chimique de France, vol. 6. pp. 920-924, 1986.
D. Robert Coulson, "Halogen Exchange Equilibria of Chlorofluoroolefins," Journal of Fluorine Chemistry, vol. 50, pp. 77-87, 1990.

*Primary Examiner* — Jafar Parsa
(74) *Attorney, Agent, or Firm* — Wenderoth, Lind & Ponack, L.L.P.

(57) ABSTRACT

The present invention provides a process for preparing a fluorine-containing propene represented by the chemical formula $CF_3CF=CX^1X^2$, wherein $X^1$ is a hydrogen atom or chlorine atom, and $X^2$ is a fluorine atom, chlorine atom, or hydrogen atom, by reacting a halogenated propene represented by the chemical formula $CClYZCF=CX^1X^2$, wherein $X^1$ and $X^2$ are the same as above, and Y and Z may be the same or different and individually indicate a fluorine atom or chlorine atom, with anhydrous hydrogen fluoride in a gas phase in the presence of a chromium oxide or a fluorinated chromium oxide as a fluorination catalyst. The process of the present invention provides a fluorine-containing propene represented by the chemical formula $CF_3CF=CClX$, wherein X is Cl, H or F, under relatively mild conditions at a high yield.

3 Claims, No Drawings

PROCESS FOR PREPARING FLUORINE-CONTAINING PROPENE BY GAS-PHASE FLUORINATION

This application is the national phase filing of International Patent Application No. PCT/JP2009/062072, filed Jun. 25, 2009, and it claims priority of U.S. Provisional Application No. 61/084,361 filed Jul. 29, 2008 and U.S. Provisional Application No. 61/084,364 filed Jul. 29, 2008.

TECHNICAL FIELD

The present invention relates to a process for preparing a fluorine-containing propene represented by the chemical formula $CF_3CF=CX^1X^2$, wherein $X^1$ is a hydrogen atom or a chlorine atom, and $X^2$ is a fluorine atom, a chlorine atom or a hydrogen atom.

BACKGROUND ART

Among the fluorine-containing propenes represented by the chemical formula $CF_3CF=CX^1X^2$, wherein $X^1$ is a hydrogen atom or a chlorine atom, and $X^2$ is a fluorine atom, a chlorine atom or a hydrogen atom, 2,3,3,3-tetrafluoropropene represented by $CF_3CF=CH_2$ (HFC-1234yf) is a compound usable as a refrigerant. The fluorine-containing propene represented by the chemical formula $CF_3CF=CCIX$, wherein X is a chlorine atom, a fluorine atom or a hydrogen atom, is an intermediate that is useful for producing various kinds of fluorocarbons.

One example of the heretofore known methods of preparing the fluorine-containing propene represented by the chemical formula $CF_3CF=CX^1X^2$ is directly fluorinating the carbon at the allylic position of propene that has at least one halogen atom bonded to a double bonded carbon atom (see Non-Patent Literature (NPL) 1 and NPL 2 below). However, because $SbF_3$ is used as a fluorinating agent in this method, more than one equivalent weight of $SbF_3$, based on fluorine atoms, per an equivalent weight of the starting propene, is necessary. This makes the process uneconomical and incurs additional cost for the waste treatment. Furthermore, because the reaction is conducted in a liquid phase, its handling is difficult. Moreover, in the case where two or more chlorine atoms are bonded to the allylic position, when all of these chlorine atoms are substituted with fluorine atoms, decomposition may follow and the yield remarkably decreases to as low as 60% or less, requiring improvement in the yield. Further, the reaction in this method should be conducted under the application of pressure and heating, making the treatment process complicated.

Regarding the compound represented by $CF_2ClCF=CFCl$ (CFC-1214yb), there is a report that not the chlorine at the allylic position of propene but the chlorine bonded to the double bonded carbon atom is preferentially replaced with fluorine by the fluorination reaction, so that $CF_2ClCF=CF_2$ (CFC-1215yc) is formed (see Patent Literature (PTL) 1 below).

Currently, there are many reports regarding the processes for preparing a fluorine-containing propene represented by $CF_3CF=CCIX$, wherein X is Cl, H or F. Specific examples of such processes include, other than the process conducting fluorination using $SbF_3$ described above, a process wherein fluorine-containing propane is subjected to dehydrohalogenation, a process wherein fluorine-containing propane is subjected to dehalogenation (i.e., removing FCl or $Cl_2$), a process wherein a halogen in fluorine-containing propene is dislocated to form a desired object, etc. Various methods for producing $CF_3CF=CCl_2$ (CFC-1214ya) are reported, for example, subjecting $CF_3CF_2CHCl_2$ (HCFC-225ca) to dehydrofluorination (see PTL 2, PTL 3, etc.), subjecting $CF_3CFClCCl_3$ (CFC-214bc) to dechlorination (see NPL 3), exchanging chlorine with fluorine in $CF_3CCl=CCl_2$ (CFC-1213xa), $CF_3CCl=CFCl$ (CFC-1214xb), $CF_3CF=CFCl$ (CFC-1215yb) or like starting material using a chromium oxide in the presence of hexafluoropropylene (NPL 4), etc. However, in these methods, the halogen elimination is conducted after forming propane, the number of steps increases and the utilization efficiency of halogen becomes undesirably low. None of these methods achieve a satisfactory yield. In particular, in the method comprising the step of dislocating halogen, the reaction system becomes complicated because many components are involved in the reaction, resulting in very low yield.

CITATION LIST

Patent Literatures

PTL 1: WO 2008/060612 A2
PTL 2: WO 2008/060614 A2
PTL 3: Japanese Unexamined Patent Publication No.1996-169850

Non Patent Literatures

NPL 1: Journal of the American Chemical Society (1946), Vol. 68, pp. 496-7
NPL 2: Journal of the American Chemical Society (1941), Vol. 63, pp. 3478-9
NPL 3: Bulletin de la Societe Chimique de France, (6), 920-4; 1986
NPL 4: Journal of Fluorine Chemistry, 50(1), 77-87; 1990

SUMMARY OF INVENTION

Technical Problem

The present invention has been accomplished in view of the above-mentioned problems of prior art techniques, and the main object is to economically provide a novel process for preparing a fluorine-containing propene represented by the chemical formula $CF_3CF=CX^1X^2$, wherein $X^1$ is a hydrogen atom or a chlorine atom, and $X^2$ is a fluorine atom, a chlorine atom, or a hydrogen atom, under relatively mild conditions at a high yield.

Solution to Problem

The present inventors conducted extensive research to achieve the above object. As a result, the present inventors found that the objective fluorine-containing propene represented by the chemical formula $CF_3CF=CX^1X^2$ can be produced under relatively mild conditions at high yield by the following process. That is, a halogenated propene represented by the chemical formula $CCIYZCF=CX^1X^2$, wherein $X^1$ is a hydrogen atom or a chlorine atom, $X^2$ is a fluorine atom, a chlorine atom, or a hydrogen atom, and Y and Z may be the same or different and individually indicate a fluorine atom or a chlorine atom, is used as a starting material and reacted with anhydrous HF in a gas phase in the presence of a chromium oxide or a fluorinated chromium oxide as a fluorination catalyst. The present invention has been thus accomplished.

Specifically, the present invention provides the processes for preparing a fluorine-containing propene as below.

Item 1. A process for preparing a fluorine-containing propene represented by the chemical formula $CF_3CF=CX^1X^2$, wherein $X^1$ is a hydrogen atom or a chlorine atom, and $X^2$ is a fluorine atom, a chlorine atom, or a hydrogen atom;

the process comprising the step of reacting a halogenated propene represented by the chemical formula $CClYZCF=CX^1X^2$ wherein $X^1$ and $X^2$ are the same as above, and Y and Z may be the same or different and individually indicate a fluorine atom or a chlorine atom, with anhydrous hydrogen fluoride in a gas phase in the presence of a chromium oxide or a fluorinated chromium oxide as a fluorination catalyst.

Item 2. The process according to Item 1, wherein the halogenated propene represented by the chemical formula $CClYZCF=CX^1X^2$ is a compound represented by the chemical formula $CClYZCF=CH_2$, wherein Y and Z may be the same or different and individually indicate a fluorine atom or a chlorine atom.

Item 3. The process according to Item 1, wherein the halogenated propene represented by the chemical formula $CClYZCF=CX^1X^2$ is a compound represented by the chemical formula $CClYZCF=CClX$, wherein X is a fluorine atom, a chlorine atom, or a hydrogen atom, and Y and Z may be the same or different and individually indicate a fluorine atom or a chlorine atom.

Item 4. The process according to any one of Items 1 to 3, wherein the fluorination catalyst is a chromium oxide represented by the composition formula $CrO_m$, wherein m falls within the range of $1.5<m<3$; or a fluorinated chromium oxide obtained by fluorinating the chromium oxide.

Item 5. The process according to any one of Items 1 to 4, wherein the reaction temperature falls within the range of from 120 to 320° C.

In the present invention, a halogenated propene represented by the chemical formula $CClYZCF=CX^1X^2$, wherein $X^1$ is a hydrogen atom or a chlorine atom, $X^2$ is a fluorine atom, a chlorine atom, or a hydrogen atom, and Y and Z may be the same or different and individually indicate a fluorine atom or a chlorine atom, is used as a starting material.

Examples of the halogenated propenes represented by the above-mentioned chemical formula include compounds represented by the chemical formula $CClYZCF=CH_2$, wherein Y and Z may be the same or different and individually indicate a fluorine atom or a chlorine atom; compounds represented by the chemical formula $CClYZCF=CClX$, wherein X is a fluorine atom, a chlorine atom, or a hydrogen atom, and Y and Z may be the same or different and individually indicate a fluorine atom or a chlorine atom; etc.

Among these fluorine-containing propenes, specific examples of the fluorine-containing propenes represented by the chemical formula $CClYZCF=CH_2$ include $CF_2ClCF=CH_2$ (HCFC-1233yf), $CFCl_2CF=CH_2$ (HCFC-1232yf), etc. These compounds may be produced by, for example, the method disclosed in NPL 1 mentioned above. Among these compounds, HCFC-1233yf may be produced by, for example, eliminating hydrogen fluoride from $CF_2ClCF_2CH_3$ (HCFC-244cc) using KOH in the presence of a phase transfer catalyst (such as Aliquat 336 ($N^+$ ($CH_3$) (n-OC)$_3$.Cl$^-$).

Specific examples of the fluorine-containing propenes represented by the chemical formula $CClYZCF=CClX$ include $CF_2ClCF=CCl_2$ (CFC-1213ya), $CFCl_2CF=CCl_2$ (CFC-1212ya), $CF_2ClCF=CFCl$ (CFC-1214yb), etc. Among these compounds, for example, $CF_2ClCF=CCl_2$ (CFC-1213ya) and $CF_2ClCF=CFCl$ (CFC-1214yb) may be easily produced by, for example, using $CF_2ClCF_2CHCl_2$ (HCFC-224ca) and $CF_2ClCF_2CHFCl$ (HCFC-225cb), respectively, as a starting material, and eliminating hydrogen fluoride from these materials using KOH in the presence of a phase transfer catalyst (for example, Aliquat 336 ($N^+$ ($CH_3$) (n-OC)$_3$.Cl$^-$). $CFCl_2CF=CCl_2$ (CFC-1212ya) may be easily produced by, for example, a process disclosed in Japanese Unexamined Patent Publication No. 1989-298188, "Phosphorus and Sulfur and the Related Elements, 11 (3), pp 373-81, 1981", etc.

In the process of the present invention, it is necessary to react a halogenated propene represented by the chemical formula $CClYZCF=CX^1X^2$, wherein $X^1$, $X^2$, Y and Z are the same as the above, with anhydrous hydrogen fluoride in a gas phase in the presence of a chromium oxide or a fluorinated chromium oxide as a fluorination catalyst. In this method, by employing the reaction conditions as described later, the objective fluorine-containing propene represented by the chemical formula $CF_3CF=CX^1X^2$, wherein $X^1$ is a hydrogen atom or a chlorine atom, and $X^2$ is a fluorine atom, a chlorine atom, or a hydrogen atom, can be obtained in relatively mild reaction conditions at a high yield.

Among the fluorination catalysts used in the present invention, the preferable catalyst is a chromium oxide, for example, represented by the composition formula $CrO_m$, wherein m falls preferably within the range of $1.5<m<3$, more preferably $1.8 \leq m \leq 2.5$, and particularly preferably $2.0 \leq m \leq 2.3$.

One example for the preparation process of the chromium oxide is described below.

First, an aqueous solution of chromium salt (chromium nitrate, chromium chloride, chromium alum, chromium sulfate, etc.) is mixed with aqueous ammonia to form a precipitate of chromium hydroxide. For example, the precipitate of chromium hydroxide can be obtained by adding 10% aqueous ammonia to a 5.7% chromium nitrate solution dropwise in an amount of 1 to 1.2 equivalent weight of ammonia per an equivalent weight of chromium nitrate. The properties of the chromium hydroxide can be controlled by varying the reaction rate during precipitation. A higher reaction rate is preferred, because the catalytic activity can be enhanced by increasing the reaction rate. The reaction rate varies depending on the temperature of the reaction solution, procedure for mixing the aqueous ammonia (mixing speed), stirring conditions and the like. Therefore, the reaction rate can be suitably adjusted by controlling these conditions.

The precipitate is filtered, washed and dried. The drying may be conducted by, for example, air-drying at a temperature of about 70 to 200° C., preferably about 120° C., for about 1 to 100 hours, preferably about 12 hours. The product at this stage is herein referred to as a "chromium hydroxide state".

Next, the dried product is disintegrated into small particles. The rate of precipitation is preferably adjusted in such a manner that the density of the disintegrated powder (for example, having a particle size of not more than 1000 μm, and 95% of the powder having sizes between 46 to 1000 μm) falls within the range of about 0.6 to 1.1 g/ml, preferably a range of about 0.6 to 1.0 g/ml. If the density of the powder is lower than 0.6 g/ml, the strength of the resulting pellets will be undesirably low. On the other hand, if the density of the powder is higher than 1.1 g/ml, catalyst activity will be low and the pellets are prone to crack. The specific surface area of the powder may preferably be about 100 $m^2$/g or larger, and more preferably about 120 $m^2$/g or larger, after degassing at 200° C. for 80 minutes. The upper limit of the specific surface area is, for example, about 220 $m^2$/g. In the present specification, the specific surface area is measured by the BET method.

If necessary, not more than approximately 3 weight % of graphite is mixed into the thus-obtained chromium hydroxide powder. The resulting mixture was formed into pellets using a tabletting machine. The size of the pellets may be about 3.0 mm in diameter and about 3.0 mm in height. The pellets may preferably have a compressive strength (pellet strength) of about 210±40 kg/cm$^2$. If the compressive strength is unduly high, the gas contact efficiency decreases to lower the catalyst activity, and the pellets break easily. On the other hand, if the compressive strength is unduly small, the resulting pellets are liable to be powdered, making handling thereof difficult.

The resulting pellets are fired in an inert atmosphere, for example, in a nitrogen gas stream, giving amorphous chromium oxide. The firing temperature is preferably not lower than 360° C. However, because chromium oxide is crystallized at exceedingly high temperatures, it is desirable that the firing temperature be set at the highest possible temperature within the range that the crystallization of chromium oxide is avoidable. For example, the pellets may be fired at a temperature of about 380 to 460° C., preferably about 400° C., for about 1 to 5 hours, preferably about 2 hours.

The fired chromium oxide may have a specific surface area of not less than about 170 m$^2$/g, preferably not less than about 180 m$^2$/g, and more preferably not less than about 200 m$^2$/g. The upper limit of the specific surface area is generally about 240 m$^2$/g, and preferably about 220 m$^2$/g. If the specific surface area exceeds 240 m$^2$/g, the catalytic activity becomes high but the deterioration rate increases. If the specific surface area is less than 170 m$^2$/g, the catalytic activity becomes undesirably low.

Fluorinated chromium oxide can be prepared by the method disclosed in Japanese Unexamined Patent Publication No. 1993-146680. For example, fluorinated chromium oxide can be prepared by subjecting the chromium oxide obtained by the above-described method to fluorination (HF treatment) using hydrogen fluoride. The fluorination temperature may be suitably selected within a range where the water generated does not condense (for example, about 150° C. at 0.1 MPa), and the upper limit may be at a temperature where the catalyst does not crystallize due to the reaction heat. There is no limitation to the pressure during fluorination, but the fluorination may preferably be conducted at the same pressure as the pressure at which the catalyst will be used in a catalytic reaction. The fluorination temperature is, for example, in the range of about 100 to 460° C.

The surface area of the catalyst decreases as a result of the fluorination. However, the catalyst usually shows a higher activity when the specific surface area is larger. The specific surface area of the catalyst after the fluorination is preferably about 25 to 130 m$^2$/g, and more preferably about 40 to 100 m$^2$/g, but it is not limited to the above range.

The fluorination reaction of chromium oxide may be conducted by supplying hydrogen fluoride to a reaction vessel containing chromium oxide, prior to the fluorination reaction of a halogenated propene compound described later. After fluorinating the chromium oxide by this method, the fluorination reaction of the halogenated propene compound can be proceeded by supplying the halogenated propene compound, which is a starting material, to the reaction vessel.

There is no limitation to the extent of the fluorination, and, for example, the fluorinated catalyst having a fluorine content of about 10 to 30 wt % can be suitably used.

Furthermore, amorphous chromium-based catalysts disclosed in Japanese Unexamined Patent Publication No. 1999-171806 may also be usable in the present invention as chromium oxide catalysts or fluorinated chromium oxide catalysts. Specifically, these catalysts comprise an amorphous chromium compound as a main component, to which at least one metal element selected from the group consisting of indium, gallium, cobalt, nickel, zinc and aluminum is added, wherein the average valence number of chromium in the chromium compound is not less than +3.5, and not grater than +5.0.

The above-mentioned fluorination catalysts, i.e., a chromium oxide or fluorinated chromium oxide may also be supported on a carrier, such as alumina, activated carbon, etc.

In the present invention, the reaction can be generally conducted simply by supplying starting materials, i.e., a halogenated propene represented by the chemical formula $CClYZCF=CX^1X^2$ and hydrogen fluoride (HF), to the reaction vessel containing the fluorination catalyst therein.

Note that the above-mentioned starting materials may be directly supplied to the reaction vessel, or may be diluted by nitrogen, helium, argon and like inert gases.

In order to maintain the long term catalytic activity, the above-mentioned starting materials may be supplied to the reaction vessel with oxygen. In this case, the amount of the oxygen supplied is generally about 0.1 to 20 mol %, and preferably about 0.1 to 5 mol % with respect to total number of moles of the halogenated propene and hydrogen fluoride, which are used as starting materials.

The proportion of the halogenated propene represented by the chemical formula $CClYZCF=CX^1X^2$ to the hydrogen fluoride may be determined based on the number of chlorine atoms bonded to the carbon atom at the allylic position of the halogenated propene, i.e., the carbon atom adjacent to the double bond and to which Y and Z are bonded. Specifically, by using the number of chlorine atoms bonding to the carbon atom at the allylic position of the propene compound as a base, hydrogen fluoride may be supplied in an amount of one or more equivalent weight of hydrogen fluoride per an equivalent weight of the halogenated propene. Based on the number of chlorine atoms bonding to the carbon atom at the allylic position of the propene compound, hydrogen fluoride may generally be supplied in an amount of about 1 to 4 equivalent weight of hydrogen fluoride per an equivalent amount of the halogenated propene.

There is no limitation to the form of the reaction vessel used in the fluorination reaction, and examples of usable reaction vessels include an adiabatica reaction vessel in which a catalyst is placed, a multitubular reaction vessel that is cooled using a cooling medium, etc. It is preferable that the reaction vessel be formed of a material resistant to the corrosive action of hydrogen fluoride, such as HASTELLOY®, INCONEL®, and MONEL®.

The fluorination reaction temperature is preferably about 120 to 320° C., and more preferably about 150 to 250° C. as the temperature in the reaction vessel. If the reaction temperature exceeds the upper limit of this temperature range, the amount of the highly fluorinated reaction product increases, decreasing the selectivity of $CF_3CF=CX^1X^2$. If the reaction temperature is lower than the lower limit of this temperature range, the starting material conversion rate is undesirably decreased.

There is no limitation to the pressure during the reaction, and the reaction may be conducted under atmospheric pressure (ordinary pressure) or the application of pressure. Specifically, the fluorination reaction of the present invention can be conducted under atmospheric pressure (0.1 MPa), but also may be conducted under the application of pressure of not greater than about 1.0 MPa.

There is no particular limitation to the reaction time, and it can be selected in such a manner that the contact time represented by W/Fo, i.e., the ratio of the weight of the catalyst used W (g) relative to the total flow rate Fo (the flow rate: cc/sec at 0° C. and 0.1 MPa) of the starting material gases (i.e., the halogenated propene and hydrogen fluoride) that are supplied to the reaction system, is generally about 1 to 15 g·sec/cc, and preferably about 2 to 8 g·sec/cc.

At the outlet of the reaction vessel, a reaction product containing a compound represented by the chemical formula $CF_3CF=CX^1X^2$, wherein $X^1$ and $X^2$ are the same as above, is obtained. Specifically, when a fluorine-containing propene represented by the chemical formula $CClYZCF=CH_2$ is used as a starting material, a reaction product containing $CF_3CF=CH_2$ (HFC-1234yf) can be obtained. When $CFCl_2CF=CCl_2$ (CFC-1212ya) is used as a starting material, a reaction product containing $CF_3CF=CCl_2$ (CFC-1214ya) can be obtained. When $CF_2ClCF=CCl_2$ (CFC-1213ya) is used as a starting material, a reaction product containing $CF_3CF=CCl_2$ (CFC-1214ya) can be obtained. When $CF_2ClCF=CFCl$ (CFC-1214yb) is used as a starting material, a reaction product containing $CF_3CF=CFCl$ (CFC-1215yb) can be obtained. When $CF_2ClCF=CClH$ (HCFC-1223yd) is used as a starting material, a reaction product containing $CF_3CF=CClH$ (HCFC-1224yd) can be obtained.

The reaction product may be collected after being purified by distillation or other method, or may be directly supplied to the subsequent step. Furthermore, unreacted starting material may be returned to the reaction vessel after the isolation and purification, so that it can be used as a starting material again. As described above, by recycling the unreacted starting material, even if the conversion rate of the starting material is low, a high productivity can be maintained.

Advantageous Effects of Invention

The production process of the present invention provides a fluorine-containing propene represented by the chemical formula $CF_3CF=CX^1X_2$, wherein $X^1$ and $X^2$ are the same as above, at a high yield under relatively mild conditions without requiring a complicated treatment step and waste disposal attributable to the use of a fluorinating agent, etc.

DESCRIPTION OF EMBODIMENTS

The present invention is explained in further detail below with reference to the Examples.

Example 1

A catalyst (9.0 g, fluorine content of about 15.0 wt %) obtained by fluorinating a chromium oxide represented by the composition formula $CrO_{2.0}$ was placed in a tubular reaction vessel made of HASTELLOY®, having an inside diameter of 15 mm and a length of 1 m. This reaction tube was maintained at atmospheric pressure (0.1 MPa) and a temperature of 250° C. Anhydrous hydrogen fluoride (HF) was supplied to the reaction vessel at 60 cc/min (the flow rate at 0° C. and 0.1 MPa, this also applies to the following Examples) for one hour. Thereafter, substantially pure $CF_2ClCF=CH_2$ (HCFC-1233yf) was supplied at 30 cc/min, and the temperature of the reaction vessel was changed to 200° C. The molar ratio of HF relative to HCFC-1233yf was 2, and the contact time (W/F$_0$) was 6.0 g·sec/cc. One hour after the reaction temperature reached a predetermined point, an outflow from the reaction vessel was analyzed using gas chromatography. Table 1 shows the results.

The composition formulae of the resulting products are as below;

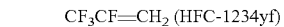

$CF_3CF=CH_2$ (HFC-1234yf)

$CF_3CF_2CH_3$ (HFC-245cb)

$CF_3CCl=CH_2$ (HCFC-1233xf)

Example 2

An experiment was conducted in the same manner as in Example 1 except that the amount of the catalyst used was changed to 12.0 g, the flow rate of the anhydrous hydrogen fluoride (HF) was changed to 90 cc/min, and the reaction temperature was changed. The molar ratio of HF relative to HCFC-1233yf was 3, and the contact time (W/F$_0$) was 6.0 g·sec/cc. Table 1 shows the results of the analysis.

Example 3

An experiment was conducted in the same manner as in Example 1 except that the amount of the catalyst used was changed to 12.0 g, and the reaction temperature was changed. The molar ratio of HF relative to HCFC-1233yf was 2, and the contact time (W/F$_0$) was 8.0 g·sec/cc. Table 1 shows the results of the analysis.

Example 4

An experiment was conducted in the same manner as in Example 1 except that the amount of the catalyst used was changed to 6.0 g, and the reaction temperature was changed. The molar ratio of HF relative to HCFC-1233yf was 2, and the contact time (W/F$_0$) was 4.0 g·sec/cc. Table 1 shows the results of the analysis.

Comparative Example 1

An experiment was conducted in the same manner as in Example 2 except that the reaction temperature was changed to 350° C. The molar ratio of HF relative to HCFC-1233yf was 3, and the contact time (W/F$_0$) was 6.0 g·sec/cc. Table 1 shows the results of the analysis.

TABLE 1

| | Ex. 1 | Ex. 2 | Ex. 3 | Ex. 4 | Comp. Ex. 1 |
|---|---|---|---|---|---|
| Reaction temperature (° C.) | 200 | 202 | 179 | 252 | 350 |
| HCFC-1233yf conversion rate(%) | 94.8 | 96.8 | 93.2 | 98.9 | 100 |
| Product selectivity(%) | | | | | |
| HFC-1234yf | 98.1 | 96.5 | 99.4 | 92.6 | 67.5 |
| HFC-245cb | 1.8 | 3.4 | 0.5 | 5.9 | 19.5 |
| HCFC-1233xf | | | | 1.3 | 8.9 |
| Others | 0.1 | 0.1 | 0.1 | 0.2 | 4.1 |

Example 5

A catalyst (12.5 g, fluorine content of about 15.0 wt %) obtained by fluorinating a chromium oxide represented by the composition formula $CrO_{2.0}$ was placed in a tubular reaction vessel made of HASTELLOY®, having an inside diameter of 15 mm and a length of 1 m. This reaction tube was maintained at atmospheric pressure (0.1 MPa) and a temperature of 250°

C. Anhydrous hydrogen fluoride (HF) was supplied to the reaction vessel at 120 cc/min for one hour. Thereafter, substantially pure CFCl$_2$CF=CH$_2$ (HCFC-1232yf) was supplied at 30 cc/min, and the temperature of the reaction vessel was changed to 201° C. The molar ratio of HF relative to HCFC-1232yf was 4, and the contact time (W/F$_0$) was 5.0 g·sec/cc. One hour after the reaction temperature reached a predetermined point, an outflow from the reaction vessel was analyzed using gas chromatography. Table 2 shows the results.

The composition formulae of the reaction products are as below;

CF$_2$ClCF=CH$_2$ (HCFC-1233yf)

CF$_3$CF=CH$_2$ (HFC-1234yf)

CF$_3$CF$_2$CH$_3$ (HFC-245cb)

CF$_3$CCl=CH$_2$ (HCFC-1233xf)

Example 6

An experiment was conducted in the same manner as in Example 5 except that the amount of the catalyst used was changed to 20.0 g, and the reaction temperature was changed. The molar ratio of HF relative to HCFC-1232yf was 4, and the contact time (W/F$_0$) was 8.0 g·sec/cc. Table 2 shows the results of the analysis.

Example 7

An experiment was conducted in the same manner as in Example 5 except that the amount of the catalyst used was changed to 10.0 g, and the reaction temperature was changed. The molar ratio of HF relative to HCFC-1232yf was 4, and the contact time (W/F$_0$) was 4.0 g·sec/cc. Table 2 shows the results of the analysis.

TABLE 2

|  | Ex. 5 | Ex. 6 | Ex. 7 |
| --- | --- | --- | --- |
| Reaction temperature (° C.) | 201 | 182 | 251 |
| HCFC-1232yf conversion rate(%) | 97.8 | 98.4 | 99.0 |
| Product selectivity(%) |  |  |  |
| HCFC-1233yf | 2.1 | 3.9 | 0.6 |
| HFC-1234yf | 96.9 | 95.6 | 92.5 |
| HFC-245cb | 0.9 | 0.5 | 5.9 |
| HCFC-1233xf |  |  | 0.8 |
| Others | 0.1 |  | 0.2 |

Example 8

A catalyst (7.5 g, fluorine content of about 15.0 wt %) obtained by fluorinating a chromium oxide represented by the composition formula CrO$_{2.0}$ was placed in a tubular reaction vessel made of HASTELLOY®, having an inside diameter of 15 mm and a length of 1 m. This reaction tube was maintained at atmospheric pressure (0.1 MPa) and a temperature of 250° C. Anhydrous hydrogen fluoride (HF) was supplied to the reaction vessel at 60 cc/min for one hour. Thereafter, substantially pure CF$_2$ClCF=CCl$_2$ (CFC-1213ya) was supplied at 30 cc/min, and the temperature of the reaction vessel was changed to 200° C. The molar ratio of HF relative to CFC-1213ya was 2, and the contact time (W/F$_0$) was 5.0 g·sec/cc. One hour after the reaction temperature reached a predetermined point, an outflow from the reaction vessel was analyzed using gas chromatography. Table 3 shows the results.

The composition formulae of the reaction products are as below;

CF$_3$CF=CCl$_2$ (CFC-1214ya)

CF$_3$CHFCFCl$_2$ (HCFC-225eb)

CF$_3$CF=CFCl (CFC-1215yb)

CF$_3$CHFCF$_2$Cl (HCFC-226ea)

CF$_3$CHFCF$_3$ (HFC-227ea)

CF$_3$CF=CF$_2$ (FC-1216yc)

CF$_3$CF$_2$CFCl$_2$ (CFC-216cb)

CF$_3$CCl=CCl$_2$ (CFC-1213xa)

Example 9

An experiment was conducted in the same manner as in Example 8 except that the amount of the catalyst used was changed to 10.0 g, and the flow rate of the anhydrous hydrogen fluoride (HF) supplied was changed to 90 cc/min. The molar ratio of HF relative to CFC-1213ya was 3, and the contact time (W/F$_0$) was 5.0 g·sec/cc. Table 3 shows the results of the analysis.

Example 10

An experiment was conducted in the same manner as in Example 8 except that the amount of the catalyst used was changed to 9.0 g, and the reaction temperature was changed. The molar ratio of HF relative to CFC-1213ya was 2, and the contact time (W/F$_0$) was 6.0 g·sec/cc. Table 3 shows the results of the analysis.

Example 11

An experiment was conducted in the same manner as in Example 8 except that the amount of the catalyst used was changed to 10.5 g, and the reaction temperature was changed. The molar ratio of HF relative to CFC-1213ya was 2, and the contact time (W/F$_0$) was 7.0 g·sec/cc. Table 3 shows the results of the analysis.

Example 12

An experiment was conducted in the same manner as in Example 8 except that the amount of the catalyst used was changed to 6.0 g, and the reaction temperature was changed. The molar ratio of HF relative to CFC-1213ya was 2, and the contact time (W/F$_0$) was 4.0 g·sec/cc. Table 3 shows the results of the analysis.

Example 13

An experiment was conducted in the same manner as in Example 8 except that the amount of the catalyst used was changed to 5.0 g, the flow rate of the anhydrous hydrogen fluoride (HF) supplied was changed to 90 cc/min, and the reaction temperature was changed. The molar ratio of HF relative to CFC-1213ya was 3, and the contact time (W/F₀) was 2.5 g·sec/cc. Table 3 shows the results of the analysis.

Comparative Example 2

An experiment was conducted in the same manner as in Example 9 except that the reaction temperature was changed to 350° C. The molar ratio of HF relative to CFC-1213ya was 3, and the contact time (W/F₀) was 5.0 g·sec/cc. Table 3 shows the results of the analysis.

TABLE 3

|  | Ex. 8 | Ex.9 | Ex.10 | Ex.11 | Ex.12 | Ex.13 | Comp. Ex.2 |
|---|---|---|---|---|---|---|---|
| Reaction temperature (° C.) | 200 | 201 | 181 | 162 | 249 | 276 | 350 |
| CFC-1213ya conversion rate (%) | 98.8 | 99.3 | 97.8 | 95.7 | 99.9 | 100 | 100 |
| Product Selectivity (%) | | | | | | | |
| CFC-1214ya | 94.4 | 92.1 | 95.9 | 97.6 | 91.2 | 81.4 | 38.6 |
| HCFC-225eb | 1.0 | 1.3 | 1.7 | 1.1 | 0.2 | | |
| CFC-1215yb | 3.5 | 4.7 | 1.9 | 1.0 | 2.4 | 1.5 | 1.2 |
| HCFC-226ea | 0.2 | 0.4 | 0.1 | | 0.5 | 3.7 | 5.8 |
| HFC-227ea | 0.4 | 0.9 | 0.2 | 0.1 | 2.1 | 4.1 | 17.3 |
| FC-1216yc | 0.2 | 0.3 | | | 2.0 | 4.0 | 18.6 |
| CFC-216cb | | | | | 0.3 | 2.2 | 4.5 |
| CFC-1213xa | 0.1 | 0.1 | | | 1.2 | 2.8 | 9.4 |
| Others | 0.2 | 0.2 | 0.2 | 0.2 | 0.1 | 0.3 | 4.6 |

Example 14

A catalyst (10.0 g, fluorine content of about 15.0 wt %) obtained by fluorinating a chromium oxide represented by the composition formula $CrO_{2.0}$ was placed in a tubular reaction vessel made of HASTELLOY® having an inside diameter of 15 mm and a length of 1 m. This reaction tube was maintained at atmospheric pressure (0.1 MPa) and a temperature of 250° C. Anhydrous hydrogen fluoride (HF) was supplied to the reaction vessel at 120 cc/min for one hour. Thereafter, substantially pure $CFCl_2CF=CCl_2$ (CFC-1212ya) was supplied at 30 cc/min, and the temperature of the reaction vessel was changed to 200° C. The molar ratio of HF relative to CFC-1212ya was 4, and the contact time (W/F₀) was 4.0 g·sec/cc. One hour after the reaction temperature reached a predetermined point, an outflow from the reaction vessel was analyzed using gas chromatography. Table 4 shows the results.

The composition formulae of the reaction products are as below;

$CF_2ClCF=CCl_2$ (CFC-1213ya)

$CF_3CF=CCl_2$ (CFC-1214ya)

$CF_3CHFCFCl_2$ (HCFC-225eb)

$CF_3CF=CFCl$ (CFC-1215yb)

$CF_3CHFCF_2Cl$ (HCFC-226ea)

$CF_3CHFCF_3$ (HFC-227ea)

$CF_3CF=CF_2$ (FC-1216yc)

$CF_3CF_2CFCl_2$ (CFC-216cb)

$CF_3CCl=CCl_2$ (CFC-1213xa)

Example 15

An experiment was conducted in the same manner as in Example 14 except that the amount of the catalyst used was changed to 14.0 g, and the flow rate of the anhydrous hydrogen fluoride (HF) supplied was changed to 180 cc/min. The molar ratio of HF relative to CFC-1212ya was 6, and the contact time (W/F₀) was 4.0 g·sec/cc. Table 4 shows the results of the analysis.

Example 16

An experiment was conducted in the same manner as in Example 14 except that the amount of the catalyst used was changed to 15.0 g, and the reaction temperature was changed. The molar ratio of HF relative to CFC-1212ya was 4, and the contact time (W/F₀) was 6.0 g·sec/cc. Table 4 shows the results of the analysis.

Example 17

An experiment was conducted in the same manner as in Example 14 except that the amount of the catalyst used was changed to 7.5 g, and the reaction temperature was changed. The molar ratio of HF relative to CFC-1212ya was 4, and the contact time (W/F₀) was 3.0 g·sec/cc. Table 4 shows the results of the analysis.

Comparative Example 3

An experiment was conducted in the same manner as in Example 15 except that the reaction temperature was changed to 349° C. The molar ratio of HF relative to CFC-1212ya was 6, and the contact time (W/F₀) was 4.0 g·sec/cc. Table 4 shows the results of the analysis.

TABLE 4

|  | Ex. 14 | Ex. 15 | Ex. 16 | Ex. 17 | Comp. Ex. 3 |
|---|---|---|---|---|---|
| Reaction temperature (° C.) | 200 | 200 | 177 | 248 | 350 |
| CFC-1212ya conversion rate (%) | 97.8 | 99.1 | 96.4 | 99.4 | 100 |
| Product selectivity % | | | | | |
| CFC-1213ya | 4.4 | 4.8 | 9.3 | 0.2 | |
| CFC-1214ya | 89.2 | 86.5 | 88.5 | 88.3 | 49.5 |
| HCFC-225eb | 1.2 | 1.8 | 0.9 | 0.2 | |
| CFC-1215yb | 3.8 | 4.5 | 0.8 | 1.2 | 1.0 |
| HCFC-226ea | 0.3 | 0.6 | 0.1 | 1.8 | 7.8 |
| HFC-227ea | 0.5 | 1.0 | 0.2 | 3.3 | 11.8 |
| FC-1216yc | 0.2 | 0.4 | 0.1 | 3.4 | 17.1 |
| CFC-216cb | | | | 0.3 | 3.2 |
| CFC-1213xa | 0.1 | 0.1 | | 0.9 | 4.8 |
| Others | 0.3 | 0.3 | 0.1 | 0.4 | 4.8 |

Example 18

A catalyst (7.5 g, fluorine content of about 15.0 wt %) obtained by fluorinating a chromium oxide represented by the composition formula $CrO_{2.0}$ was placed in a tubular reaction vessel made of HASTELLOY®, having an inside diameter of 15 mm and a length of 1 m. This reaction tube was maintained at atmospheric pressure (0.1 MPa) and a temperature of 250°

C. Anhydrous hydrogen fluoride (HF) was supplied to the reaction vessel at 60 cc/min for one hour. Thereafter, substantially pure $CF_2ClCF=CFCl$ (CFC-1214yb) was supplied at 30 cc/min, and the temperature of the reaction vessel was changed to 200° C. The molar ratio of HF relative to CFC-1214yb was 2, and the contact time (W/F$_0$) was 5.0 g·sec/cc. One hour after the reaction temperature reached a predetermined point, an outflow from the reaction vessel was analyzed using gas chromatography. Table 5 shows the results. The composition formulae of the reaction products are as below;

$CF_3CF=CFCl$ (CFC-1215yb)

$CF_3CHFCF_2Cl$ (HCFC-226ea)

$CF_3CF=CF_2$ (FC-1216yc)

$CF_3CHFCF_3$ (HFC-227ea)

$CF_3CCl=CFCl$ (CFC-1214xb)

Example 19

An experiment was conducted in the same manner as in Example 18 except that the amount of the catalyst used was changed to 10.0 g, and the flow rate of the anhydrous hydrogen fluoride (HF) supplied was changed to 90 cc/min. The molar ratio of HF relative to CFC-1214yb was 3, and the contact time (W/F$_0$) was 5.0 g·sec/cc. Table 5 shows the results of the analysis.

Example 20

An experiment was conducted in the same manner as in Example 18 except that the amount of the catalyst used was changed to 10.5 g, and the reaction temperature was changed. The molar ratio of HF relative to CFC-1214yb was 2, and the contact time (W/F$_0$) was 7.0 g·sec/cc. Table 5 shows the results of the analysis.

Example 21

An experiment was conducted in the same manner as in Example 18 except that the amount of the catalyst used was changed to 6.0 g, and the reaction temperature was changed. The molar ratio of HF relative to CFC-1214yb was 2, and the contact time (W/F$_0$) was 4.0 g·sec/cc. Table 5 shows the results of the analysis.

TABLE 5

|  | Ex. 18 | Ex. 19 | Ex. 20 | Ex. 21 |
|---|---|---|---|---|
| Reaction temperature ° C.) | 200 | 199 | 175 | 251 |
| CFC-1214yb conversion rate (%) | 98.4 | 99.0 | 96.6 | 99.8 |
| Product selectivity (%) |  |  |  |  |
| CFC-1215yb | 94.8 | 91.8 | 96.6 | 90.3 |
| HCFC-226ea | 0.9 | 1.5 | 1.4 | 2.4 |
| FC-1216yc | 2.9 | 4.7 | 1.7 | 3.2 |
| HFC-227ea | 1.2 | 1.8 | 0.2 | 2.6 |
| CFC-1214xb | 0.1 | 0.1 |  | 1.3 |
| Others | 0.1 | 0.1 | 0.1 | 0.2 |

The invention claimed is:

1. A process for preparing a fluorine-containing propene represented by the chemical formula $CF_3CF=CX^1X^2$, wherein $X^1$ is a hydrogen atom or a chlorine atom, and $X^2$ is a fluorine atom, a chlorine atom, or a hydrogen atom;

the process comprising the step of reacting at least one halogenated propene selected from the group consisting of $CF_2ClCF=CCl_2$, $CFCl_2CF=CCl_2$ and a compound represented by the chemical formula $CClYZCF=CH_2$, wherein Y and Z may be the same or different and individually represent a fluorine atom or a chlorine atom, with anhydrous hydrogen fluoride in a gas phase in the presence of a chromium oxide or a fluorinated chromium oxide as a fluorination catalyst, wherein the fluorine-containing propene obtained by the process is $CF_3CF=CCl_2$ when $CF_2ClCF=CCl_2$ or $CFCl_2CF=CCl_2$ is the halogenated propene, and the fluorine-containing propene obtained by the process is $CF_2ClCF=CH_2$ when the compound represented by the chemical formula $CClYZCF=CH_2$ is the halogenated propene.

2. The process according to claim 1, wherein the fluorination catalyst is a chromium oxide represented by the composition formula $CrO_m$, wherein m falls within the range of $1.5<m<3$; or a fluorinated chromium oxide obtained by fluorinating the chromium oxide.

3. The process according to claim 1, wherein the reaction temperature falls within the range of 120 to 320° C.

* * * * *